US012629218B2

(12) United States Patent
Mustufa et al.

(10) Patent No.: US 12,629,218 B2
(45) Date of Patent: May 19, 2026

(54) SYSTEMS AND METHODS FOR DISPLAYING AN INSTRUMENT NAVIGATOR IN A TELEOPERATIONAL SYSTEM

(71) Applicant: INTUITIVE SURGICAL OPERATIONS, INC., Sunnyvale, CA (US)

(72) Inventors: Tabish Mustufa, Sunnyvale, CA (US); Benjamin S. Flamm, Palo Alto, CA (US); Paul A. Hoover, Bothell, WA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1437 days.

(21) Appl. No.: 16/316,747

(22) PCT Filed: Apr. 25, 2017

(86) PCT No.: PCT/US2017/029400
§ 371 (c)(1),
(2) Date: Jan. 10, 2019

(87) PCT Pub. No.: WO2018/013198
PCT Pub. Date: Jan. 18, 2018

(65) Prior Publication Data
US 2019/0151032 A1 May 23, 2019

Related U.S. Application Data

(60) Provisional application No. 62/362,381, filed on Jul. 14, 2016.

(51) Int. Cl.
*A61B 1/00* (2006.01)
*A61B 34/00* (2016.01)
(Continued)

(52) U.S. Cl.
CPC .......... *A61B 34/25* (2016.02); *A61B 1/00149* (2013.01); *A61B 1/00193* (2013.01);
(Continued)

(58) Field of Classification Search
CPC ......... A61B 34/25; A61B 34/20; A61B 34/30; A61B 34/35; A61B 90/00; A61B 90/37;
(Continued)

(56) References Cited

U.S. PATENT DOCUMENTS

| | | | |
|---|---|---|---|
| 5,471,541 A | | 11/1995 | Burtnyk et al. |
| 5,836,869 A | * | 11/1998 | Kudo ................. A61B 1/00009 |
| | | | 600/173 |

(Continued)

FOREIGN PATENT DOCUMENTS

| | | |
|---|---|---|
| KR | 20160010426 A | 1/2016 |
| WO | WO-2009158164 A1 | 12/2009 |

OTHER PUBLICATIONS

International Preliminary Report on Patentability for Application No. PCT/US2017/029400, mailed on Jan. 24, 2019, 9 pages.
(Continued)

*Primary Examiner* — Michael J Carey
*Assistant Examiner* — William B Chou
(74) *Attorney, Agent, or Firm* — Haynes & Boone, LLP.

(57) ABSTRACT

A system comprises a teleoperational assembly including a teleoperational manipulator coupled to a plurality of instruments in a surgical environment. The system also comprises a processing unit including one or more processors. The processing unit is configured to display a first synthetic rendering of the plurality of instruments, recognize a triggering event, and change from displaying the first synthetic rendering to displaying a second synthetic rendering of the plurality of instruments in response to recognition of the triggering event.

19 Claims, 6 Drawing Sheets

(51) Int. Cl.

| | |
|---|---|
| *A61B 34/20* | (2016.01) |
| *A61B 34/30* | (2016.01) |
| *A61B 34/35* | (2016.01) |
| *A61B 90/00* | (2016.01) |
| *G06T 3/60* | (2024.01) |

(52) U.S. Cl.
CPC .............. *A61B 34/20* (2016.02); *A61B 34/30* (2016.02); *A61B 34/35* (2016.02); *A61B 90/00* (2016.02); *A61B 90/37* (2016.02); *G06T 3/60* (2013.01); *A61B 2034/254* (2016.02); *A61B 2034/301* (2016.02); *A61B 2090/365* (2016.02); *A61B 2090/371* (2016.02); *A61B 2090/373* (2016.02)

(58) Field of Classification Search
CPC .............. A61B 1/00149; A61B 1/0019; A61B 2034/254; A61B 2034/301; A61B 2090/365; A61B 2090/371; A61B 2090/373; G06T 3/60
See application file for complete search history.

(56) References Cited

U.S. PATENT DOCUMENTS

| | | | | |
|---|---|---|---|---|
| 6,234,958 | B1 * | 5/2001 | Snoke | A61B 1/303 600/114 |
| 6,493,608 | B1 | 12/2002 | Niemeyer et al. | |
| 6,636,254 | B1 * | 10/2003 | Onishi | G06T 3/60 348/65 |
| 6,671,581 | B2 | 12/2003 | Niemeyer et al. | |
| 6,817,974 | B2 | 11/2004 | Cooper et al. | |
| 8,377,045 | B2 | 2/2013 | Schena et al. | |
| 9,043,018 | B2 * | 5/2015 | Mohr | A61B 34/71 606/1 |
| 2004/0254454 | A1 | 12/2004 | Kockro | |
| 2005/0203380 | A1 | 9/2005 | Sauer et al. | |
| 2006/0258938 | A1 * | 11/2006 | Hoffman | A61B 5/06 600/424 |
| 2008/0118115 | A1 | 5/2008 | Williamson et al. | |
| 2008/0183071 | A1 * | 7/2008 | Strommer | A61B 5/062 382/128 |
| 2009/0010508 | A1 * | 1/2009 | Inoue | G06T 7/50 382/128 |
| 2009/0192524 | A1 | 7/2009 | Itkowitz et al. | |
| 2009/0326553 | A1 | 12/2009 | Mustufa et al. | |
| 2011/0071473 | A1 | 3/2011 | Rogers et al. | |
| 2015/0038981 | A1 | 2/2015 | Kilroy et al. | |
| 2015/0272694 | A1 * | 10/2015 | Charles | G16H 40/63 600/202 |
| 2015/0297300 | A1 | 10/2015 | Gomez et al. | |
| 2016/0220324 | A1 * | 8/2016 | Tesar | A61B 90/20 |
| 2017/0071688 | A1 * | 3/2017 | Cohen | A61B 1/05 |
| 2017/0143442 | A1 * | 5/2017 | Tesar | H04N 23/63 |
| 2018/0324414 | A1 * | 11/2018 | Hoffman | A61B 34/30 |
| 2018/0325604 | A1 * | 11/2018 | Atarot | A61B 5/7475 |
| 2019/0142528 | A1 * | 5/2019 | Vertikov | A61B 1/00172 600/424 |
| 2025/0040789 | A1 * | 2/2025 | Nir | A61B 1/042 |

OTHER PUBLICATIONS

International Search Report and Written Opinion for Application No. PCT/US2017/029400, mailed on Aug. 7, 2017, 15 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

400

420

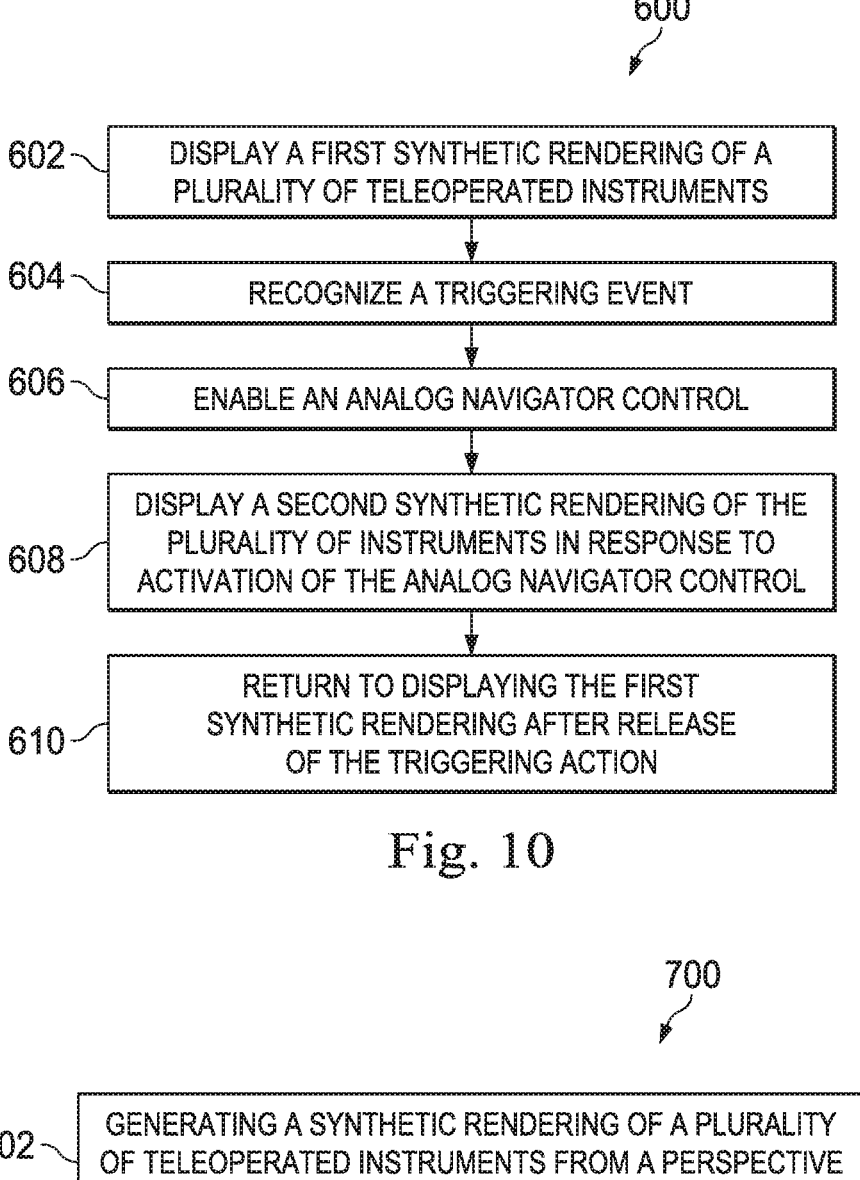

600

602 — DISPLAY A FIRST SYNTHETIC RENDERING OF A PLURALITY OF TELEOPERATED INSTRUMENTS

604 — RECOGNIZE A TRIGGERING EVENT

606 — ENABLE AN ANALOG NAVIGATOR CONTROL

608 — DISPLAY A SECOND SYNTHETIC RENDERING OF THE PLURALITY OF INSTRUMENTS IN RESPONSE TO ACTIVATION OF THE ANALOG NAVIGATOR CONTROL

610 — RETURN TO DISPLAYING THE FIRST SYNTHETIC RENDERING AFTER RELEASE OF THE TRIGGERING ACTION

702 — GENERATING A SYNTHETIC RENDERING OF A PLURALITY OF TELEOPERATED INSTRUMENTS FROM A PERSPECTIVE DISTAL OF THE PLURALITY OF INSTRUMENTS

704 — LATERALLY INVERT THE SYNTHETIC RENDERING OF THE PLURALITY OF INSTRUMENTS

706 — DISPLAY THE LATERALLY INVERTED SYNTHETIC RENDERING OF THE PLURALITY OF INSTRUMENTS

Fig. 11

SYSTEMS AND METHODS FOR DISPLAYING AN INSTRUMENT NAVIGATOR IN A TELEOPERATIONAL SYSTEM

RELATED APPLICATIONS

This patent application is the U.S. national phase of International Application No. PCT/US2017/029400, filed Apr. 25, 2017, which designated the U.S. and claims priority to and the benefit of the filing date of U.S. Provisional Patent Application 62/362,381, entitled "SYSTEMS AND METHODS FOR DISPLYAING AN INSTRUMENT NAVIGATOR IN A TELEOPERATIONAL SYSTEM," filed Jul. 14, 2016, all of which are incorporated by reference herein in their entirety.

TECHNICAL FIELD

The present disclosure is directed to systems and methods for performing a, teleoperated medical procedure and more particularly to systems and methods for displaying synthetically rendered views of instruments in a surgical environment to assist the user in understanding instrument configuration.

BACKGROUND

Medical robotic systems such as teleoperative systems used to perform minimally invasive medical techniques are intended to reduce the amount of tissue that is damaged during invasive medical procedures, thereby reducing patient recovery time, discomfort, and harmful side effects. Examples of teleoperative systems include the da Vinci® Surgical System and the da Vinci® S™ Surgical System from intuitive Surgical, Inc., of Sunnyvale, Calif. Each of these systems includes a surgeon's consoler a patient-side cart, a high performance three-dimensional ("3-D") vision system, and Intuitive Surgical's proprietary EndoWrist® articulating instruments, which are modeled after the human wrist. When added to the motions of manipulators holding the surgical instruments, these articulating instruments allow at least six degrees of freedom of motion to their end effectors, which is comparable to or even greater than the natural motions of open surgery. During the performance of a medical procedure, it is useful to view two or three dimensional live images of the surgical site captured by an image capturing device. Often the image provided by the image capturing device may provide the user with insufficient information to understand the configuration of the surgical instruments. Accordingly, the image from the image capturing device may be supplemented with one or more renderings of the instruments that allow the user to understand the instrument configurations.

SUMMARY

The embodiments of the invention are best summarized by the claims that follow the description.

Consistent with some embodiments, a system comprises a teleoperational assembly including a teleoperational manipulator coupled to a plurality of instruments in a surgical environment. The system also comprises a processing unit including one or more processors. The processing unit is configured to display a first synthetic rendering of the plurality of instruments, recognize a triggering event, and change from displaying the first synthetic rendering to displaying a second synthetic rendering of the plurality of instruments in response to recognition of the triggering event.

Consistent with some embodiments, a system comprises a teleoperational assembly including a teleoperational manipulator coupled to a plurality of instruments in a surgical environment and a processing unit including one or more processors. The processing unit is configured to generate a synthetic rendering of the plurality of instruments from a perspective distal of the plurality of instruments, laterally invert the synthetic rendering of the plurality of instruments, and display the laterally inverted synthetic rendering of the plurality of instruments.

Consistent with some embodiments, a method performed by a computer processing system comprises displaying a first synthetic rendering of a plurality of instruments. The plurality of instruments is coupled to a teleoperational manipulator of a teleoperational assembly. The method also comprises recognizing a triggering event and changing from displaying the first synthetic rendering to displaying a second synthetic rendering of the plurality of instruments in response to recognition of the triggering event.

Consistent with some embodiments, a method performed by a computer processing system comprises generating a synthetic rendering of a plurality of instruments from a perspective distal of the plurality of instruments. The plurality of instruments are coupled to a teleoperational manipulator of a teleoperational assembly. The method further comprises laterally inverting the synthetic rendering of the plurality of instruments and displaying the laterally inverted synthetic rendering of the plurality of instruments.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

FIG. 10 illustrates a method for displaying an instrument navigator rending according to some embodiments.

FIG. 11 illustrates a method for displaying an instrument navigator rending according to some embodiments.

DETAILED DESCRIPTION

Figure 1:
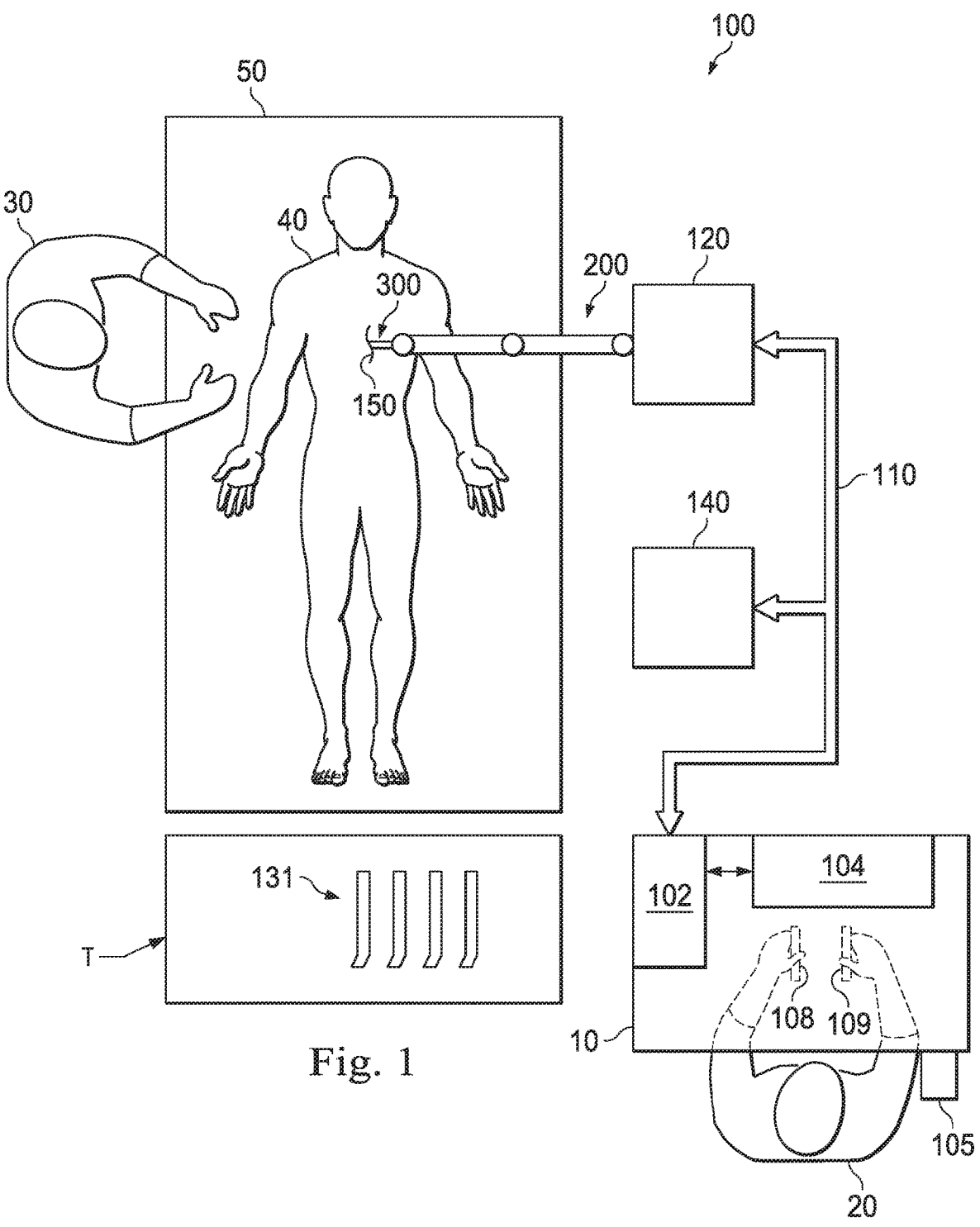
FIG. 1 is a simplified diagram of an operating room employing a teleoperated medical system with a bundled unit of medical devices according to some embodiments.

FIG. 1 illustrates, as an example, a top view of an operating room in which a teleoperational medical system 100 is being utilized by a Surgeon 20 for performing a medical procedure on a Patient 40 who is lying down on an operating table 50. One or more Assistants 30 may be positioned near the Patient 40 to assist in the procedure while the Surgeon 20 performs the procedure teleoperatively by manipulating control devices 108, 109 on a surgeon console 10.

In the present example, an entry guide 300 including a bundled unit of medical devices is inserted through a single entry port 150 into the Patient 40. Although the entry port 150 is a minimally invasive incision in the present example, in the performance of other medical procedures, it may instead be a natural body orifice. The entry guide 300 is held and manipulated by a teleoperated arm assembly 200 of a teleoperated manipulator assembly 120, which also may be referred to in some embodiments as a patient side cart. Although only one teleoperated arm assembly is used in the present example, the teleoperated medical system 100 may equipped with additional teleoperated arm assemblies.

The surgeon console 10 includes a 3-D monitor 104 for displaying a 3-D image of a surgical site to the Surgeon, left and right manipulatable control devices 108, 109, a foot pedal 105, and a control system 102. The control devices 108, 109 may include any one or more of a variety of input devices such as joysticks, gloves, trigger-guns, hand-operated controllers, or the like. The control system 102 may include a processor which may be a dedicated computer integrated into the console 10 or positioned next or near to it, or it may comprise a number of processing or controller components that are distributed in a distributed processing fashion throughout the system 100. Also provided near the Patient is an auxiliary monitor 140 to be viewed by the Assistant during the performance of the medical procedure on the Patient.

The surgeon console 10 is usually located in the same room as the Patient so that the Surgeon may directly monitor the procedure, is physically available if necessary, and is able to speak to the Assistant(s) directly rather than over the telephone or other communication medium. However, it will be understood that the Surgeon can also be located in a different room, a completely different building, or other remote location from the Patient allowing for remote surgical procedures.

Figure 3:
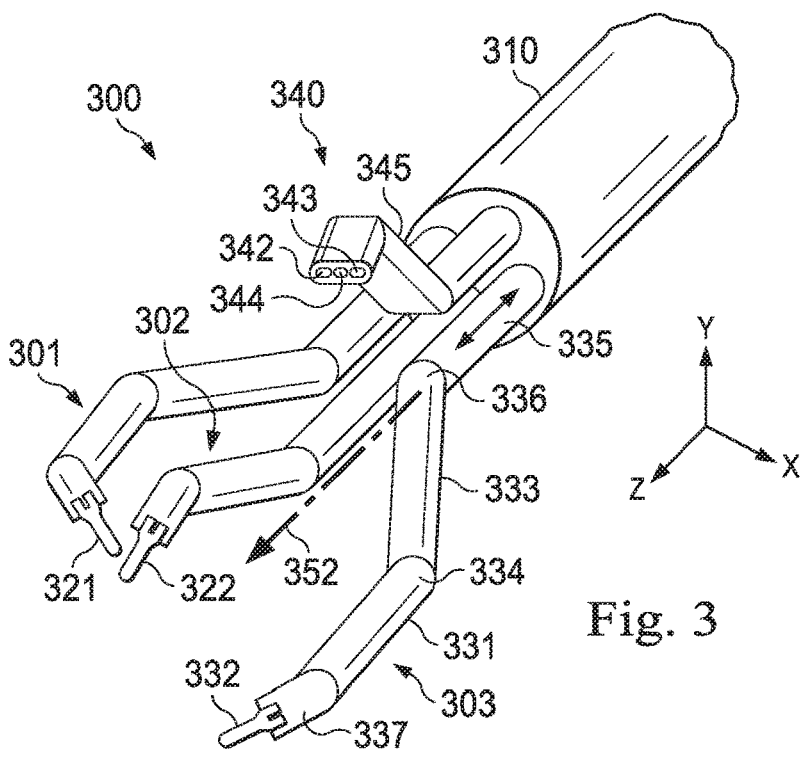
FIG. 3 is a simplified diagram of a distal end of a bundled unit of medical devices according to some embodiments.

As shown in FIG. 3, the entry guide 300 may include three surgical instruments or tools 301, 302, 303 and an image capturing device 340. Each of the surgical tools 301, 302, 303 may be associated with one of the control devices 108, 109. The Surgeon performs a medical procedure by manipulating the control devices 108, 109 so that the control system 102 causes corresponding movement of one of the associated surgical tools 301, 302, 303 while the Surgeon views the surgical site in 3-D on the console monitor 104 as it is captured by the image capturing device 340. During the medical procedure, the surgical tools may be reassigned to a different one of the control devices 108, 109.

Control devices 108, 109 may be provided with at least the same degrees of freedom as their associated tools 301, 302, 303 to provide the Surgeon with telepresence, or the perception that the control devices 108, 109 are integral with the tools 301, 302, 303 so that the Surgeon has a strong sense of directly controlling the tools.

The monitor 104 may be positioned near the Surgeon's hands so that it will display a projected image that is oriented so that the Surgeon feels that he or she is actually looking directly down onto the operating site. To that end, images of the tools 301, 302, 303 (if visible in the view of the image capturing device 340) may appear to be located substantially where the Surgeon's hands are located.

In addition, the real-time image is preferably projected into a perspective image such that the Surgeon can manipulate the respective end effectors 321, 322, 332 of the tools 301, 302, 303 through their corresponding control devices as if viewing the workspace in substantially true presence. By true presence, it is meant that the presentation of an image is a true perspective image simulating the viewpoint of an operator that is physically manipulating the tools 301, 302, 303. Thus, the control system 102 transforms the coordinates of the tools 301, 302, 303 to a perceived position so that the perspective image is the image that one would see if the image capturing device 140 was located directly behind the tools 301, 302, 303.

The control system 102 performs various functions in the system 100. One important function that it performs is to translate and transfer the mechanical motion of control devices 108, 109 to the teleoperated arm assembly 200 through control signals over bus 110 so that the Surgeon can effectively manipulate the tools 301, 302, 303.

Although described as a control system 102 is described as having a processor, it is to be appreciated that the control system 102 may be implemented in practice by any combination of hardware, software and firmware. Also, its functions as described herein may be performed by one unit or divided up among different components, each of which may be implemented in turn by any combination of hardware, software and firmware. Further, although being shown as part of or being physically adjacent to the console 10, the control system 102 may also comprise a number of subunits distributed throughout the system such as in printed circuit boards installed in the patient side cart 120 and/or the teleoperated arm assembly 200, as well as, or alternatively to, the console 10.

For additional details on the construction and operation of various aspects of a medical teleoperated system such as described herein, see, e.g., commonly owned U.S. Pat. No. 6,493,608 "Aspects of a Control System of a Minimally Invasive Surgical Apparatus," and commonly owned U.S. Pat. No. 6,671,581 "Camera Referenced Control in a Minimally Invasive Surgical Apparatus," which are incorporated herein by reference in their entireties.

Figure 2:
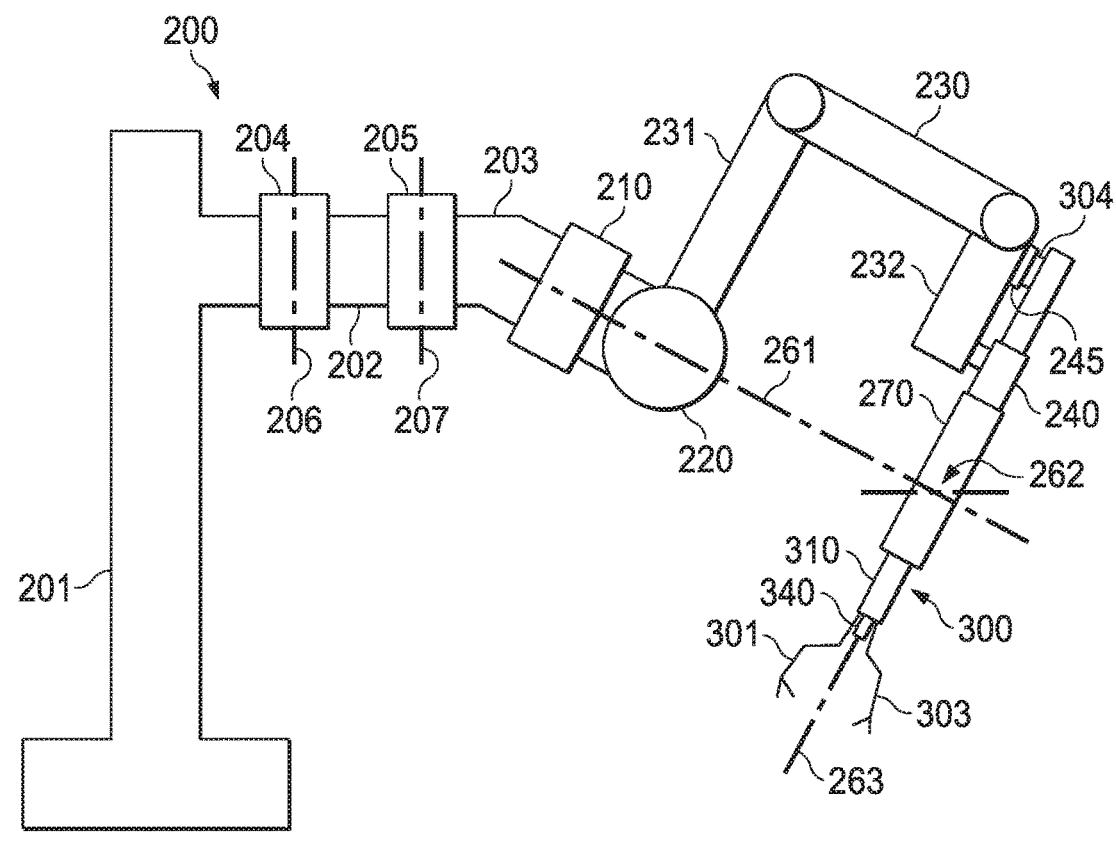
FIG. 2 is a simplified diagram of a teleoperated arm assembly holding a bundled unit of medical devices according to some embodiments.

FIG. 2 illustrates, as an example, a simplified side view (not necessarily in proportion or complete) of the teleoperated arm assembly 200 which is holding the entry guide 300. A tool guide 270 is inserted through the minimally invasive incision 150 in the Patient, and coupled to the teleoperated arm assembly 200 by a guide holder 240. The entry guide 300 may then be inserted into the Patient through the tool guide 270. The teleoperated arm assembly 200 is mechanically supported by a base 201 of the patient side cart 120.

Links 202, 203 of arm 200 are coupled together and to the base 201 through horizontal setup joints 204, 205. The setup joints 204, 205 in this example are passive joints that allow manual positioning of the arm 200 when their brakes are released. For example, setup joint 204 allows link 202 to be manually rotated about axis 206, and setup joint 205 allows link 203 to be manually rotated about axis 207.

Although only two links and two setup joints are shown in this example, more or fewer of each may be used as appropriate in this and other teleoperated arm assemblies in conjunction with the present invention. For example, although setup joints 204, 205 are useful for horizontal positioning of the arm 200, additional setup joints may be included and useful for limited vertical and angular positioning of the arm 200. For major vertical positioning of the arm 200, however, the arm 200 may also be slidably moved along the vertical axis of the base 201 and locked in position.

The teleoperated arm assembly 200 also includes two active joints and a number of gears driven by motors. A yaw joint 210 allows arm section 230 of to rotate around an axis 261, and a pitch joint 220 allows arm section 230 to rotate about an axis perpendicular to that of axis 261 and orthogonal to the plane of the drawing. An interface 304 comprises mating parts on the carriage 245 and the proximal end of the entry guide 300 such as motor driven gears that actuate movement of the surgical tools 338, 339 and image capturing unit 340 through conventional joints, cable and pulley systems.

The arm section 230 is configured so that sections 231, 232 are always parallel to each other as the pitch joint 220 is rotated by its motor. As a consequence, the entry guide 300 may be controllably moved by driving the yaw and pitch motors so as to pivot about the pivot point 262, which is generally located through manual positioning of the setup joints 204, 205 so as to be at the point of entry into the Patient. In addition, the entry guide 300 is coupled to a carriage 245 on the arm section 230 which in turn is coupled to a linear drive mechanism to extend or retract the entry guide 300 along its insertion axis 263.

Although each of the yaw joint 210, pitch joint 220 and motor driven gears in the carriage 245 is controlled by an individual joint or gear controller, the controllers may be controlled by a common master/slave control system so that the medical devices of the entry guide 300 may be controlled through user e.g., Surgeon or operator) manipulation of its associated control device.

FIG. 3 illustrates, as an example, a perspective view of a distal end of the entry guide 300. The entry guide 300 includes removable surgical tools 301, 302, 303 for performing a medical procedure and a removable image capturing unit 340 for viewing the procedure at a surgical site within a patient. Although three removable surgical tools are shown, more or fewer surgical tools may be implemented in alternative embodiments. Each of the tools 301, 302, 303 and image capturing unit 340 extends through a separate lumen formed in an inner core of the entry guide 300. Replacement of one or both of the surgical tools 301, 302, 303 during or in preparation for performing a medical procedure may then be accomplished by the Assistant removing the tool that is no longer needed from its lumen and replacing it with a substitute tool 131 from a tray T by inserting the substitute tool 131 in the vacated lumen. Alternatively, if unused lumens are available, an additional tool may be inserted through one of those available lumens without removing any other tools already in place.

The image capturing device 340 preferably includes a stereoscopic pair of cameras 342, 343 (and/or a single binocular camera) for three-dimensional imaging of the surgical site and an illuminating device 344 such as a light emitting diode (LED) or a fiber optics bundle carrying light from an external source, to enhance visibility of objects in the captured images. Auxiliary image capturing units, such as an ultrasound probe, may also be provided in available lumens of the entry guide 300 for "seeing" into anatomic structures for surgical or diagnostic purposes.

In some embodiments, a cannula or overtube 310 is also included in the entry guide 300 for protecting its inner core and the medical devices (i.e., surgical tools and image capturing units) inserted therethrough. The overtube 310 may be rigid. Alternatively, it may be formed of flexible material or comprise actively and/or passively bendable sections so that the over tube 310 may conform to the shapes of body lumens as it moves therethrough to a surgical site within a patient.

The surgical tools 301, 302, 303 each have a controllably extendable, rotatable, and bendable arm to which their respective end effectors 321, 322, 332 are coupled to by a wrist mechanism. For example, the surgical tool 303 comprises three links 331, 333, 335 coupled by distal joints 334, 336 and a wrist mechanism 327 coupling the end effector 332. The proximal link 335 is controllably extendable and retractable along a longitudinal axis 352 (which is generally parallel to the insertion axis 263 of the single-port device 300), and is controllably rotatable about the insertion axis 352. The middle link 333, on the other hand, is controllably bendable by distal joint 336 relative to the link 335, and the distal link 331 is coupled to the links 333, 335 and bendable by distal joint 334 so that its bend angle is in an opposite direction as that of the link 333 and consequently, keeps links 331, 335 in parallel alignment.

The arms of the surgical tools 301, 302 are similarly constructed as that of the surgical tool 303. Additional details for one example of the wrist mechanism 327 are provided in commonly owned U.S. Pat. No. 6,817,974 "Surgical Tool Having Positively Positionable Tendon-Actuated Multi-Disk Wrist Joint," which is incorporated herein by this reference.

The image capturing device 340 also has a controllably extendable, rotatable, and bendable arm 345 that facilitates at least insertion/retraction of the image capturing unit 340 along its longitudinal axis (which may be parallel to the insertion axis 263 of the single-port device 300) and pitch motion in order to achieve a sufficient elevation of the image capturing device 340 "above" the surgical tools 338, 339 so as to properly view them during a surgical procedure. Additional degrees of freedom, such as roll angular movement of the image capturing device 340 about its insertion axis, may also be provided in order to facilitate additional positioning and orientation capabilities for the image capturing device 340. For enhanced maneuverability, the image capturing arm 345 may also be bendable such as the controllably bendable, rotatable, and extendable arms of the surgical tools 301, 302, 303.

The entry guide 300 operates in a surgical environment referenced by an X-Y-Z coordinate system in which the longitudinal axes of the tools 301, 302, 303 are generally aligned with the Z-axis.

Figure 4:
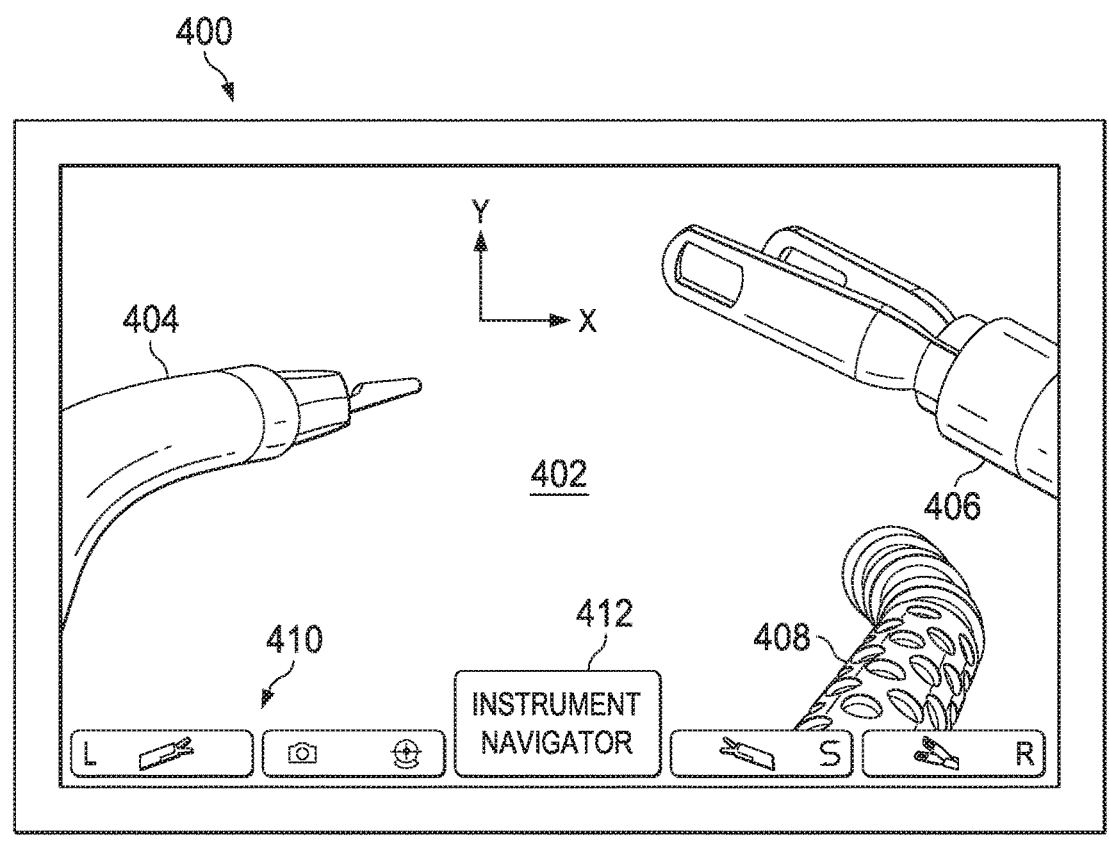
FIG. 4 illustrates a field of view of a surgical environment with an instrument navigator rendering according to some embodiments.

FIG. 4 is a display 400 of a surgical environment inside a patient anatomy (e.g., Patient 40). The display 400 may be presented, for example on one or both of the monitors 104, 140. An imaging instrument (e.g., imaging instrument 340) is used to generate an image 402 of the imaging instrument's field of view within the surgical environment. The image 402 may be a three dimensional image obtained by a stereoscopic endoscope and generated as a composite image of the images visible to a user through right and left eye displays. The surgical environment coordinate system is defined such that the Z-axis extends generally perpendicular, into and out of the plane of the image 402. The field of view includes an image of a distal end portion of an instrument 404, a distal end portion of instrument 406, and a distal end portion of instrument 408. Instruments 404, 406, 408 may be the same or substantially similar to tools 301, 302, 303. The display 400 also includes information fields 410 located at the periphery of the image 402 which may include instructions to the clinician, warnings, instrument identification information, status information, or other information relevant to the surgical procedure.

The display 400 also includes an instrument navigator 412 which provides a synthetic rendering of the distal ends of the instruments 404, 406, 408. The instrument navigator 412 is rendered from the perspective of a virtual camera positioned in the surgical environment to allow the Surgeon 20 to visualize the configuration of the instruments and to visualize instruments that may be outside the field of view of the imaging instrument providing the image 402. The navigator is superimposed or otherwise graphically integrated or presented with the image 402. The instrument navigator 412 may be synthetically rendered using information from the teleoperational system 100 such as kinematic information about the teleoperated arm assembly and instruments (e.g., known lengths of rigid components and commanded, sensed or otherwise known orientations of joints) and/or sensor information about the position and orientation of the entry guide and instruments. Synthetic renderings of auxiliary instrument images are disclosed in U.S. patent application Ser. No. 12/163,087, "Medical robotic system providing an auxiliary view of articulatable instruments extending out of a distal end of an entry guide," which is incorporated herein by reference in its entirety.

Figure 5:
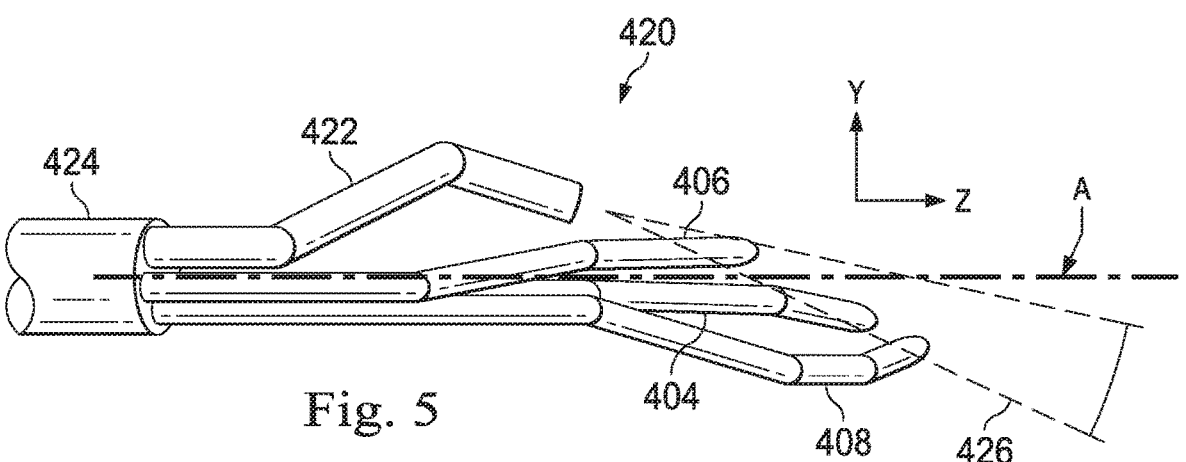
FIG. 5 illustrates a side view of an instrument navigator rendering according to some embodiments.

FIG. 5 illustrates an instrument navigator 420. Instrument navigator 420 is a synthetic instrument rendering from the perspective of a virtual camera positioned in a Y-Z plane parallel to a longitudinal axis A. This perspective is generally transverse to perspective of the imaging instrument 340. Axis A extends through the entry guide that includes the instruments 404, 406, 408 and art image capture instrument 422 (e.g. device 340), all extending front cannula 424. In this example, navigator 420 is considered to be a side view of the entry guide. The navigator 420 also illustrates the field of view 426 of the image capture device 422 to assist the viewer with reconciling the image 402 and the navigator 420. The perspective of the navigator 420 provides visualization of instrument depth and movement in the Z-direction and up/down position and motion in the Y-direction, but provides little information about movement in the X-direction. This perspective may also obscure some of the instruments such as instrument 404 on the opposite side of the instrument bundle.

Figures 6, 7:
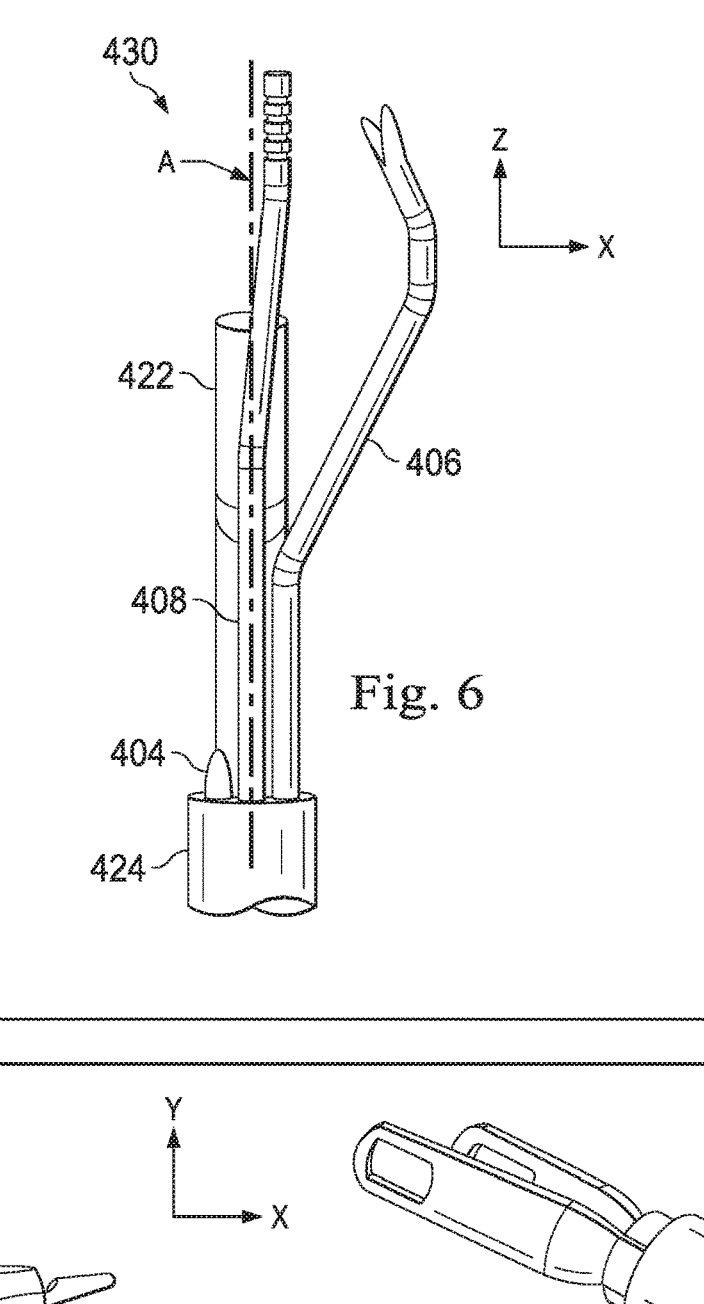
FIG. 6 illustrates an under side view of an instrument navigator rendering according to some embodiments.
FIG. 7 illustrates a field of view of a surgical environment with an instrument navigator rendering according to some embodiments.

FIG. 6 illustrates art instrument navigator 430. Instrument navigator 430 is a synthetic instrument rendering from the perspective of a virtual camera positioned in an X-Z plane parallel to the longitudinal axis A. This perspective is generally transverse to perspective of the imaging instrument 340. In this example, the image from the virtual camera is laterally inverted about the Z-axis (i.e. flipped about the Z-axis) to generate the synthetic instrument rendering 430. The inversion of the image maintains the left-right orientation of the instruments in correspondence with the instruments in the camera image 402. The navigator 430 is considered to be a mirrored underside view of the entry guide. The perspective of the navigator 430 provides visualization of instrument depth and movement in the Z-direction and lateral position and motion in the X-direction, but provides little information about movement in the Y-direction.

In an alternative example, a synthetic rendering of a top side view instrument navigator may be generated from the perspective of a virtual camera positioned in an X-Z plane parallel to the longitudinal axis A at a 180° rotation about the Z-axis from the perspective of the virtual camera generating underside navigator 430. This perspective is also generally transverse to perspective of the imaging instrument 340. In this example, the image from the virtual camera is not laterally inverted about the Z-axis. The perspective of the top side view navigator also provides visualization of instrument depth and movement in the Z-direction and lateral position and motion in the X-direction, but provides little information about movement in the Y-direction. This perspective may also obscure some of the instruments such as instrument on the opposite side of the instrument bundle.

Each of these two dimensional viewpoints (i.e. navigators 420, 430) obscures one or more of the instruments and provides limited information about a third dimension of movement, so allowing the viewer to alternate between the two navigators may provide more complete information about the three dimensional movement and position of the instruments. The navigators may be alternated based upon a fully manual triggering event such as activating a manual switch at the surgeon console 10 to toggle between navigators. Repeated analog inputs such as switch activation may become laborious for the Surgeon 20, so other types of navigators that provide views of all of the bundled instruments in a two dimensional single view and other techniques for alternating views that require fewer user inputs may improve the user experience and provide more useful information for conducting the medical procedure.

Figure 8:
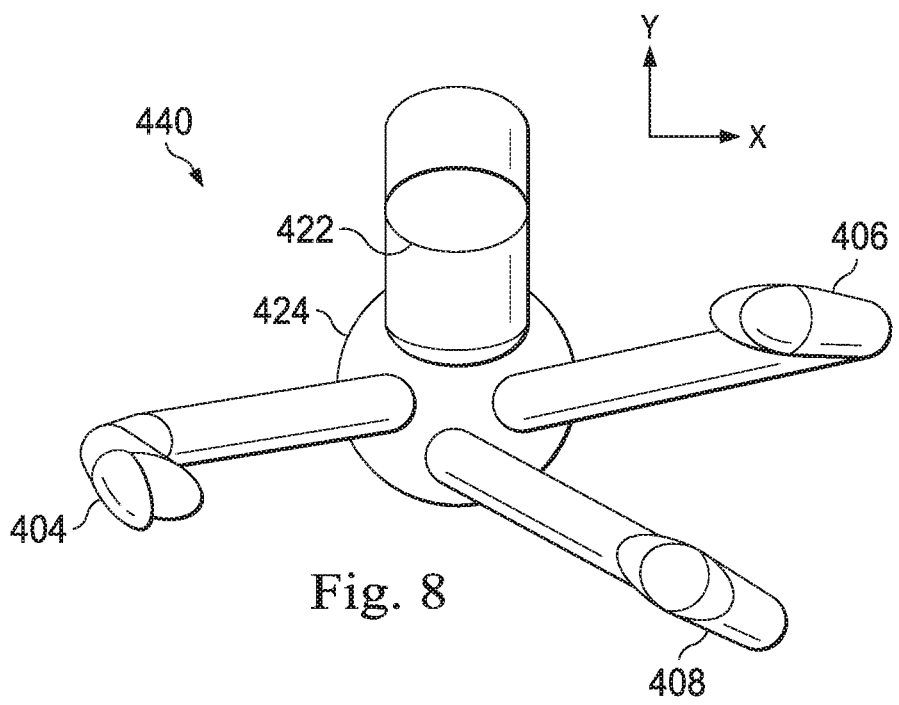
FIG. 8 illustrates the instrument navigator rendering of FIG. 7 in greater detail.

FIG. 7 illustrates the display 400 of FIG. 4 with an instrument navigator 440, shown in greater detail in FIG. 8. Instrument navigator 440 is a synthetic instrument rendering from the perspective of a virtual camera positioned in an X-Y plane distal of the instruments along the longitudinal axis A. In this example, the image from the virtual camera is laterally inverted about the Y-axis (i.e. flipped about the Y-axis) to generate the synthetic instrument rendering 440. Thus, the navigator 420 is considered to be a mirrored front view of the entry guide. In this mirrored view, all four instruments 404, 406, 408, 422 are visible. Additionally, the inversion of the image maintains the left-right orientation of the instruments in correspondence with the instruments in the camera image 402. The perspective of the navigator 440 provides visualization of the instrument's up/down position and motion in the Y-direction and also provides visualization of the instrument's lateral position and motion in the X-direction. However, this perspective may provide little information about instrument movement in the Z-direction.

To provide the Surgeon 20 with a full set of information about the position, orientation, and movement of the instruments, different navigator renderings may be provided in response to user input or the current system state and/or operational mode.

Figure 9:
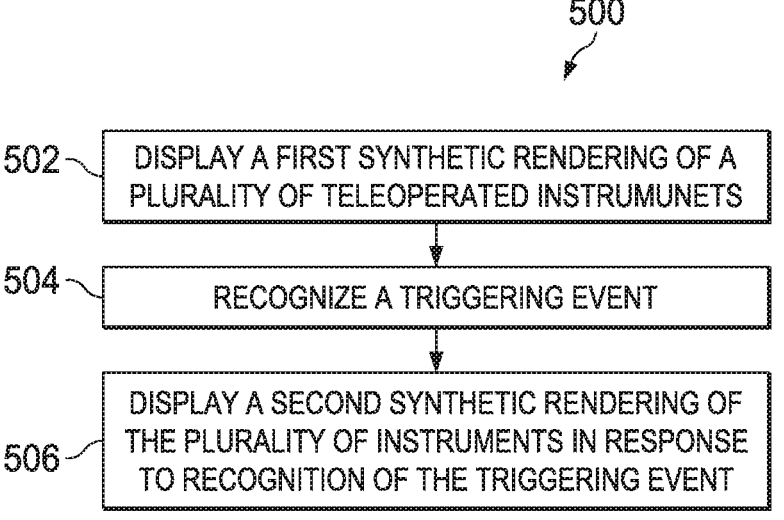
FIG. 9 illustrates a method for displaying an instrument navigator rending according to some embodiments.

FIG. 9 illustrates a method 500 for displaying an instrument navigator rendering according to some embodiments. The method 500 is illustrated as a set of operations or processes 502-506. Not all of the illustrated processes 502-506 may be performed in all embodiments of method 500. Additionally, one or more processes that are not expressly illustrated in FIG. 9 may be included before, after, in between, or as part of the processes 502-508. In some embodiments, one or more of the processes 502-508 are optional and may be omitted.

At a process 502, a synthetic rendering of the plurality of the teleoperated instruments is displayed on a display device. The synthetic rendering may be, for example, the front, mirror-view navigator 440, a side view navigator 420 or an overhead view navigator 430. In some embodiments, the default navigator provided as the first synthetic rendering may be the navigator 440. At a process 504, a triggering event is recognized by the teleoperational system 100. The triggering event may be a user input at the surgeon's console 10 such as activation of a manual switch, depressing a foot pedal, a voice command or other user input.

Alternatively, the triggering event may be a change in the system state such as a change in operational mode. The teleoperational system 100 may include a variety of operational modes including an instrument control mode in which movement of the user inputs 108, 109 directly control movement of one or more of the instruments. The system 100 may also include a clutch mode in which master/slave control of the instruments is suspended and manual reconfiguration of the manipulator assembly may be performed by the Assistant 30. The system 100 may also include a guided tool change mode in which one or more of the instruments are exchanged. The system 100 may also include camera adjust and relocation modes in which the entry guide 300 and the attached instruments are moved. The system 100 may also include a camera control mode in which only the imaging instrument of the entry guide 300 is movable.

At a process 506, in response to the triggering event, a different synthetic rending of a navigator may be displayed. Optionally, when a subsequent triggering event is recognized, the system may display the first navigator or a different navigator from either the first or second navigators.

As an example of the method 500, when the teleoperational system is in the common operational master/slave instrument control mode, the default navigator may be the front, mirror-view navigator 440. When the teleoperational system transitions to a clutch or guided tool change mode, the navigator may change to the navigator 430 to provide the Surgeon with information about movement in the Z-direction and to allow the Surgeon to visualize instruments that may be outside of the imaging instrument field of view. Transitioning to the navigator 430 allows the Surgeon to maintain left-right orientation, however in alternative embodiments, in which left-right orientation is less important, the navigator 420 may instead be displayed. When the teleoperational system transitions back to the instrument control mode, the mode change may be detected and the navigator changes back to the navigator 440.

In an alternative example of the method 500, multiple conditions may need to be met before changing from the default navigator. For example, when the teleoperational system is in the common master/slave instrument control mode, the default navigator may be the front, mirror-view navigator 440. When the teleoperational system transitions to one of the camera adjust, relocation or control modes, the navigator may maintain the navigator 440 until a second event is recognized. The second event may be the recognition, by the teleoperational system, that at least one instrument is outside of the imaging instrument field of view. Only when both conditions are met (i.e., entry into a camera mode and recognition that the instrument is out of view), the navigator is changed from navigator 440 to the navigator 430 to provide the Surgeon with information about movement in the Z-direction and to allow the Surgeon to visualize instruments that may be outside of the imaging instrument field of view. When the teleoperational system transitions back to the instrument control mode or the instruments all enter the field of view, the mode and status change are detected and the navigator changes back to the navigator 440.

FIG. 10 illustrates a method 600 for displaying an instrument navigator rendering according to some embodiments. The method 600 is illustrated as a set of operations or processes 602-608. Not all of the illustrated processes 602-608 may be performed in all embodiments of method 600. Additionally, one or more processes that are not expressly illustrated in FIG. 10 may be included before, after, in between, or as part of the processes 602-608. In some embodiments, one or more of the processes 602-608 are optional and may be omitted.

At a process 602, a synthetic rendering of the plurality of the teleoperated instruments is displayed on a display device. The synthetic rendering may be, for example, the front, mirror-view navigator 440, a side view navigator 420, an under side view navigator 430 or a top side view navigator. In some embodiments, the default navigator provided as the first synthetic rendering may be the navigator 440. At a process 604, a triggering event is recognized by the teleoperational system 100. The triggering event may be, for example, a change in the system state such as a change in operational mode as described above.

At a process 606, an analog navigator control is enabled in response to the recognition of the triggering event. The analog navigator control may be, for example a rotary knob, a linear slider, or other type of control at the surgeon's console 10 that allows for a smooth, continuous transition between different navigators.

At a process 608, in response to an activation of the enabled analog navigator control, a different synthetic rendering of a navigator may be displayed. This second rendering is a blend between the first and an alternate navigator view, which is adjusted continuously by the analog navigator control. In one alternative embodiment, this continuous transition may be achieved by smoothly moving the position of the virtual camera between two navigator views. Thus, in this example, the triggering event alone does not cause an immediate display of the second navigator. Both the triggering event and activation of the enabled navigator control are prerequisites for the display of the second navigator. Optionally, at a process 610, the analog navigator control may have a return feature such that when the analog navigator control is released, the control springs back to the default initial position. When the analog navigator control returns to the default initial position, the display changes back to the first synthetic rendering. The analog navigator control may be bi-directional to, for example, allow the Surgeon to toggle between left and right side view navigators. In one alternative embodiment, the analog navigator control action may be a motion of the user input device 108, 109 about the roll axis.

FIG. 11 illustrates a method 700 for displaying an instrument navigator rending according to some embodiments. The method 700 is illustrated as a set of operations or processes 702-706. Not all of the illustrated processes 702-706 may be performed in all embodiments of method 700. Additionally, one or more processes that are not expressly illustrated in FIG. 10 may be included before, after, in between, or as part of the processes 702-706. In some embodiments, one or more of the processes 702-706 are optional and may be omitted.

At a process 702, a synthetic rendering of the plurality of the teleoperated instruments is generated from a perspective distal of the instruments. At a process 704, the generated synthetic rendering is laterally inverted. At a process 706, the laterally inverted synthetic rendering is displayed. One example of the method 700 is used to create the display of the front, mirror-view navigator 440. The initial synthetic rendering is from the perspective of a virtual camera positioned in an X-Y plane distal of the instruments and perpendicular to the longitudinal axis A. This initial rendering is laterally inverted or flipped about a Y-axis to provide a more intuitive mirrored-view in which the left right orientation of the instruments in the camera image 402 and the navigator 440 are the same.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
a teleoperational assembly including a teleoperational manipulator coupled to a plurality of instruments in a surgical environment; and
a processing unit including one or more processors, wherein the processing unit is configured to
display a synthetic rendering of the plurality of instruments,
recognize a triggering event comprising a change in an operational state of the teleoperational assembly from a first operational state to a second operational state, wherein movement of a control device causes movement of at least one of the plurality of instruments in only one of the first or second operational states, and change a perspective associated with displaying the synthetic rendering of the plurality of instruments in response to recognition of the triggering event.

2. The system of claim 1 wherein the at least one of the plurality of instruments is movable along a central longitudinal axis of the at least one of the plurality of instruments in response to the movement of the control device.

3. The system of claim 1 wherein the processing unit is further configured to enable an analog control at a user console of the teleoperational assembly and change the perspective associated with displaying the synthetic rendering in response to activation of the enabled analog control.

4. The system of claim 1 wherein the perspective associated with displaying the synthetic rendering without recognition of the triggering event is distal of the plurality of the instruments and provides a mirrored and laterally inverted view of the plurality of instruments.

5. The system of claim 4 wherein the perspective associated with displaying the synthetic rendering without recognition of the triggering event is from a perspective plane along a central longitudinal axis through the plurality of instruments.

6. The system of claim 1 wherein the perspective associated with displaying the synthetic rendering in response to recognition of the triggering event is perpendicular to the perspective of associated with displaying the synthetic rendering without recognition of the triggering event.

7. The system of claim 1 wherein the perspective associated with displaying the synthetic rendering in response to recognition of the triggering event is from a perspective plane parallel to a central longitudinal axis through the plurality of instruments.

8. The system of claim 1 wherein at least one of the plurality of instruments is an imaging instrument.

9. The system of claim 8 wherein the processing unit is further configured to display an image of a field of view of the surgical environment captured by the imaging instrument.

10. The system of claim 9 wherein the synthetic rendering is displayed in a common display window with the image of the field of view.

11. The system of claim 9 wherein at least one of the plurality of instruments is not visible in the image of the field of view.

12. The system of claim 1 wherein the synthetic rendering of the plurality of instruments is generated based on instrument poses of each of the plurality of instruments determined by the teleoperational assembly.

13. A system comprising:
a teleoperational assembly including a teleoperational manipulator coupled to a plurality of instruments in a surgical environment, the plurality of instruments configured as a bundled unit in an entry guide insertable through a single entry port; and
a processing unit including one or more processors, wherein the processing unit is configured to
generate a synthetic rendering of the plurality of instruments from a perspective distal of a distal end of at least one of the plurality of instruments and along a central longitudinal axis of the bundled unit,
laterally invert the synthetic rendering of the plurality of instruments, and
display the laterally inverted synthetic rendering of the plurality of instruments.

14. The system of claim 13 wherein at least one of the plurality of instruments is an imaging instrument.

15. The system of claim 14 wherein the processing unit is further configured to display an image of a field of view of the surgical environment captured by the imaging instrument.

16. The system of claim 15 wherein the synthetic rendering is displayed in a common display window with the image of the field of view.

17. The system of claim 15 wherein at least one of the plurality of instruments is not visible in the image of the field of view.

18. The system of claim 13 wherein the synthetic rendering of the plurality of instruments is generated based on instrument poses of each of the plurality of instruments determined by the teleoperational assembly.

19. A system comprising:
  a teleoperational assembly including a teleoperational manipulator coupled to a plurality of instruments in a surgical environment; and a processing unit including one or more processors, wherein the processing unit is configured to:
    display a synthetic rendering of the plurality of instruments from a perspective of a first virtual camera;
    recognize a triggering event comprising a change in an operational state of the teleoperational assembly from a first operational state to a second operational state, wherein movement of a control device causes movement of at least one of the plurality of instruments in only one of the first or second operational states; and
    change the displaying of the synthetic rendering of the plurality of instruments to a perspective of a second virtual camera in response to recognition of the triggering event.

\* \* \* \* \*